United States Patent
Carella et al.

(10) Patent No.: US 8,389,325 B2
(45) Date of Patent: Mar. 5, 2013

(54) SELECTIVE FUNCTIONALIZATION BY JOULE EFFECT THERMAL ACTIVATION

(75) Inventors: Alexandre Carella, Mazeres Lezons (FR); Jean-Pierre Simonato, Sassenage (FR)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 0 days.

(21) Appl. No.: 13/180,754

(22) Filed: Jul. 12, 2011

(65) Prior Publication Data
US 2012/0012901 A1    Jan. 19, 2012

(30) Foreign Application Priority Data
Jul. 19, 2010   (FR) ..................... 10 55863

(51) Int. Cl.
*H01L 51/40*  (2006.01)
*H01L 21/302*  (2006.01)

(52) U.S. Cl. .............. 438/99; 438/780; 257/E51.04; 257/E51.038

(58) Field of Classification Search .......... 438/99, 438/780; 257/E51.04, E51.038
See application file for complete search history.

(56) References Cited

U.S. PATENT DOCUMENTS

| | | | | |
|---|---|---|---|---|
| 5,063,081 | A * | 11/1991 | Cozzette et al. | 435/4 |
| 7,112,816 | B2 * | 9/2006 | Schlaf et al. | 257/24 |
| 7,927,888 | B2 * | 4/2011 | Buckley et al. | 438/1 |
| 8,163,633 | B2 * | 4/2012 | Korgel et al. | 438/492 |
| 2011/0171789 | A1 * | 7/2011 | Korgel et al. | 438/151 |
| 2012/0018301 | A1 * | 1/2012 | Joshi et al. | 204/403.14 |
| 2012/0025330 | A1 * | 2/2012 | Lim et al. | 257/414 |

FOREIGN PATENT DOCUMENTS

| | | |
|---|---|---|
| FR | 2 262 300 A1 | 9/1975 |
| FR | 2 934 685 A1 | 2/2010 |

OTHER PUBLICATIONS

Search Report for French Patent Application No. 10 55863, dated Feb. 22, 2011.
Buriak, J. M., et al.; "Lewis Acid Mediated Functionalization of Porous Silicon with Substituted Alkenes and Alkynes"; Journal of American Chemistry; vol. 120; Feb. 1, 1998; pp. 1339-1340; XP002920673.
Clavaguera, S., et al.; "Sub-ppm Detection of Nerve Agents Using Chemically Functionalized Silicon Nanoribbon Field-Effect Transistors"; Angewandte Chemie International Edition; vol. 49; Issue 24; Apr. 30, 2010; pp. 4063-4066; XP002623524.
Cui, Y., et al.; "Nanowire nanosensors for highly sensitive and selective detection of biological and chemical species"; *Science*; Aug. 17, 2001, vol. 293; Issue 5533, pp. 1289-1292.
Evrard, D., et al.; "Electrochemical Functionalization of Carbon Surfaces by Aromatic Azide or Alkyne Molecules: A Versatile Platform for Click Chemistry"; Chemistry—A European Journal; vol. 14; Issue 30; Sep. 9, 2008; pp. 9286-9291; XP002623524.

(Continued)

*Primary Examiner* — Ngan Ngo
(74) *Attorney, Agent, or Firm* — Alston & Bird LLP

(57) ABSTRACT

The invention relates to a method for functionalizing a conductive or semiconductor material (M) by covalent grafting of receptor molecules (R) to its surface, said method comprising the following steps: (i) applying, across the terminals of a source electrode and a drain electrode located on either side of the material (M), sufficient potential difference to thermally activate the material (M) with respect to the grafting reaction of the molecules (R); and (ii) placing the material (M) thus activated in contact with a liquid or gaseous medium containing receptor molecules (R), thereby obtaining a material (M) functionalized by covalently grafted receptor molecules (R).

11 Claims, 1 Drawing Sheet

OTHER PUBLICATIONS

Park, I., et al.; "Multifunctional Nanowire Array for Chemical Sensing and Manipulation"; Solid-State Sensors, Actuators and Microsystems Conference, 2009. Transducers 2009. International; IEEE; Piscataway, New Jersey; Jun. 2009; pp. 473-476.

Park, I., et al., "Selective surface functionalization of silicon nanowires via nanoscale Joule heating"; Nano Letters; vol. 7; Oct. 2007; pp. 3106-3111.

Prades, J.D., et al.; "Ultralow power consumption gas sensors based on self-heated individual nanowires"; Applied Physics Letters; vol. 93; Issue 12; Sep. 24, 208; pp. 123110-1-123110-3; XP012111599.

Zhou, X.T., et al.; "Silicon nanowires as chemical sensors", Chemical Physics Letters; vol. 369; Issues 1-2; Feb. 7, 2003; pp. 220-224.

* cited by examiner

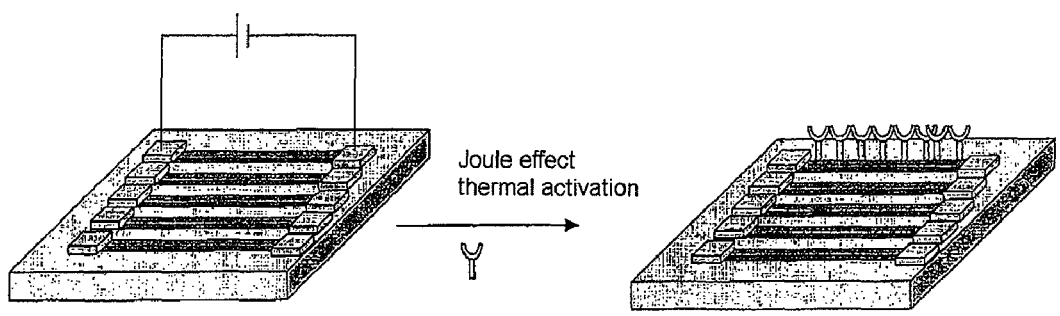

SELECTIVE FUNCTIONALIZATION BY JOULE EFFECT THERMAL ACTIVATION

FIELD OF THE INVENTION

The present invention relates to a method for selectively functionalizing conductive or semiconductor materials, to the materials obtained using this method, and to the use of these materials in devices for detecting and/or quantifying molecules of interest (chemical sensors).

BACKGROUND

Nanowire-based chemical sensors have, in the last few years, excited great interest, leading to many developments being reported in the literature. In particular, sensors using silicon nanowires have been described for detecting the pH of a solution of proteins (Cui, Y.; Wei, Q.; Park, H.; Lieber, C. M.; Science, 2001, 293, 1289-1292), or else gas molecules (Zhou, X. T.; Hu, J. Q.; Li, C. P.; Ma, D. D.; Lee, C. S.; Lee, S. T.; Chem. Phys. Lett., 2003, 369, 220-224) and other molecules of interest. The detection mechanism of these silicon-nanowire-based sensors is generally based on a change in the electrical conductivity of these nanowires in the presence of charged chemical molecules or biological molecules on their surface.

Detection of these target molecules is generally made possible only after an appropriate chemical functionalization of the surface of the silicon nanowires with "probe" molecules capable of interacting specifically with the target molecules to be detected. Most of the time, these sensors take the form of matrices in which the selective functionalization of the nanowires is vital.

Several methods aiming to localize the surface functionalization have been described in the literature, in particular: methods based on electrostatic attraction between the probe molecules (or receptor molecules) and the nanowire: photolithography of a hydrophobic film; microcontact printing; dip pen nanolithography; and electrochemical methods.

However, the electrostatic-attraction-based method does not allow a high selectivity for the surface modification to be obtained relative to the surrounding areas and may not be used to graft neutral or weakly charged receptor molecules.

The photolithographic and microcontact printing methods do not allow ultrafine, especially nanoscale, localization.

Furthermore, printing techniques also require a precise alignment of the prefabricated micro/nano structures. Dip pen nanolithography provides excellent flexibility in terms of localization of the selective surface functionalization and in terms of the molecules that can be grafted. However, this technique requires the use of expensive equipment, and it is not suitable for surface functionalization on a large scale. Finally, electrochemical methods are limited by the choice of functional groups, which must have redox properties.

More recently, a method for selectively functionalizing silicon nanowires using the Joule effect has been reported. More precisely, this method is based on the very localized nanoscale Joule heating that occurs when an electric field is applied across the terminals of a silicon nanowire (Inkyu Park; Zhiyong Li; Albert P. Pisano and R. Stanley Williams; Nano Leu., 2007, 7 (10), pp 3106-3111). This very localized heating can be used to selectively remove a protective polymer film that covers a preselected region of a silicon nanowire. After appropriate subsequent processing, the surface thus exposed can then be functionalised by chemical molecules, whereas the other neighbouring regions of the nanowire remain protected by the chemically inert polymer film.

However, this surface functionalization method requires a prior step of coating the silicon nanowires with a polymer film and then, optionally, a step of removing the protective polymer film once the surface functionalization has been carried out.

SUMMARY

A new method has now been developed allowing the surface of a conductive or semiconductor material to be selectively functionalized on the nanoscale. More precisely, this method uses thermal energy, generated locally by Joule heating, to activate the conductive or semiconductor material with respect to chemical reactions.

Thus, when a potential difference is applied to the terminals of two electrodes located on either side of a semiconductor material such as a silicon nanowire, part of the electrical energy is converted into thermal energy by Joule heating. The nanowire is then converted into a resistor, locally heating the solution or the gas containing the receptor molecule(s) to be grafted.

Advantageously, this method allows a very selective surface functionalization in that only the electrically, and therefore thermally, activated nanowires will be functionalized by the receptor molecules.

Furthermore, this easily implemented method may be carried out in a limited number of steps. Thus, it especially does not require prior application of a polymer film on the material to be selectively functionalized. In addition, it may be easily scaled up to the industrial scale.

Thus, a first subject of the invention relates to a method for functionalizing a conductive or semiconductor material (M) by covalent grafting of receptor molecules (R) to its surface, said method comprising the following steps:

i) applying, across the terminals of a source electrode and a drain electrode located on either side of the material (M), sufficient potential difference to thermally activate the material (M) with respect to the grafting reaction of the molecules (R); and ii) placing the material (M) thus activated in contact with a liquid or gaseous medium containing receptor molecules (R), thereby obtaining a material (M) functionalized by covalently grafted receptor molecules (R).

The Conductive or Semiconductor Material (M)

According to one aspect, the material (M) is a nanomaterial, i.e. a material having at least one nanoscale morphological characteristic, i.e. a material one dimension of which is smaller than 100 nm. Mention may be made, by way of exemplary nanomaterials, of nanowires, nanosheets or nanotubes, in particular silicon nanowires and carbon nanotubes.

The material (M) may be a conductive or semiconductor material.

According to a preferred aspect, the material (M) is a semiconductor, especially a carbon-, silicon-, germanium-, zinc-, gallium-, indium- or cadmium-based material or an organic semiconductor.

According to a preferred aspect, the semiconductor is a silicon-based material, especially a material comprising or formed from one or more silicon nanowires or nanosheets, or a carbon-based material, especially a material comprising or formed from carbon nanotubes or carbon sheets.

Preferably, the material (M) is a material comprising at least 30 wt %, preferably at least 50 wt % and more preferably 75 wt % of silicon relative to the total weight of the material.

More preferably, the semiconductor material is formed from one more silicon nanowires etched on an SOI (silicon-on-insulator) surface.

According to one particularly preferable embodiment, the material (M) is a silicon nanowire located in a matrix containing several other silicon nanowires. Advantageously, the method according to the invention makes it possible to differentiate the various silicon nanowires and to selectively functionalize one or more of these nanowires.

In the case of organic semiconductors, the latter may be oligomer, polymer or small molecules organic semiconductors. For example they may be: heterocyclic aromatic compounds such as thiophenes and their derivatives, preferably P3HT (poly(3-hexylthiophene)); polypyrroles and their derivatives; arylamines and their derivatives, preferably PTA (polytriarylamine); isochromanones and their derivatives; heterocyclic macrocycles such as porphyrins; or phtalocyanines and their derivatives. The organic semiconductor materials may also be: polycyclic aromatic acenes and their derivatives, preferably anthracene or pentacene; arylenes and their derivatives, for example perylene, polyparaphenylene, poly (p-phenylene vinylene) or polyfluorene; or polysilanes and their derivatives.

Grafting Reaction of the Receptor Molecules

The expression "receptor molecule", as employed here, is understood to mean a molecule capable of interacting with a target molecule, for example a biological molecule or an analyte. The receptor molecule may especially comprise a part (A) capable of ensuring that the target molecule to be detected is recognized, and a reactive function (X) able to covalently bond with the surface of the material (M) when the latter is activated. The part (A) ensuring the specific recognition may especially comprise a polynucleotide, a polypeptide, an aptamer, a biological receptor or a ligand.

The expression "sufficient potential difference to thermally activate the material (M) with respect to the grafting reaction of the molecules (R)" is here understood to mean that the thermal energy, generated by Joule heating, heats the material (M) to a temperature (T) high enough to activate the reaction that grafts the molecules (R) onto the material (M). In step (ii) this potential difference is maintained so that the material (M), activated in step (i), is brought into contact with the medium containing the receptor molecules (R) at a temperature greater than or equal to said activation temperature (T).

Step (i) of activating the material (M) by applying said potential difference may be carried out before, after or at the same time as step (ii), i.e. contact with the medium containing the receptor molecules (R).

Preferably, the material (M) is brought into contact with a liquid medium containing the receptor molecules (R), especially a solution of (R) in an organic solvent such as mesitylene.

When the material (M) is silicon based, the grafting reaction is especially hydrosilylation i.e. a reaction adding a hydrosilane (Si—H) function to a receptor molecule comprising an unsaturated organic function X, in particular an ethylene (C=C double bond) or acetylene (C≡C triple bond) function. The grafting reaction then generally leads to a Si—C covalent bond being formed between the material (M) and the receptor molecule. The hydrosilylation may especially be activated when the material (M) locally reaches a temperature above 200° C.

Preferably, when the material is based on silicon nanowires, the absolute value of the potential difference is between 2 and 10 V, and especially about 5 V.

According to a preferred variant, the receptor molecules (R) comprise a group X chosen from —C≡C— and —HC=CH— groups, preferably an Ar—C≡C— group, where Ar represents a $C_5$-$C_{10}$ aryl. The receptor molecules are preferably chosen from ethynylferrocene and 4-ethynyltabinol.

According to another variant, the receptor molecules comprise a diazonium salt, a triazene or a diene. In this context, the receptor molecules are preferably chosen from diazoniumferrocene or 4-diazobenzyltabinol.

This is because, 4-ethynyltabinol is a receptor specifically of organophosphorus compounds. Exposing this receptor molecule to an organophosphorus compound leads to an unstable intermediate phosphate ester being formed by a reaction between the primary alcohol and the organophosphorus compound. There follows an intramolecular cyclization via nucleophilic substitution of the intermediate phosphate ester with the tertiary amine and formation of a quaternary ammonium. During the cyclization reaction a salt is formed and therefore separate electric charges (cation and anion) are generated. The generation of a charge via the creation of the ammonium function enables the electrostatic environment of the molecule to be abruptly modified. The presence of organophosphorus compounds is therefore demonstrated by visualizing the modifications to the local electrostatic environment by analyzing variations in the resistance, conductance or transconductance of an electrical device in which the "receptor" molecule is grafted onto the semiconductor material. The presence of at least one charge created by the reaction between the organophosphorus compound and the receptor molecule is detected using this electric device.

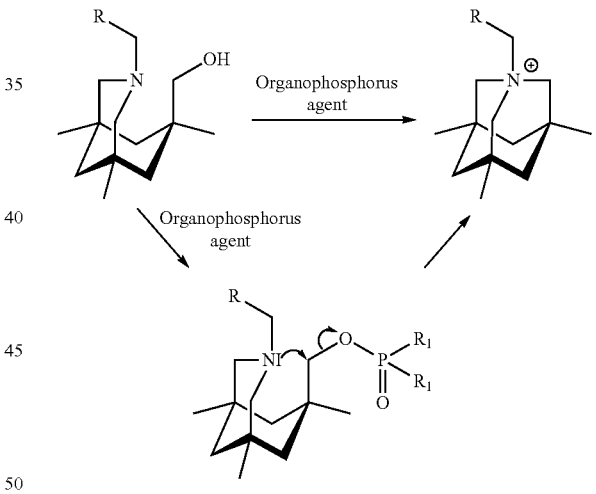

Such a device has especially been described in patent application FR 2 934 685 filed on Feb. 5, 2010.

According to a second subject, the invention relates to a conductive or semiconductor material (M) functionalized by grafting receptor functions (R) obtained using the method of the invention.

According to a third aspect, the invention relates to an electrical device (chemical sensor) comprising a drain electrode and a source electrode separated by a conductive or semiconductor material (M), in which the material (M) is a material obtained using the method of the invention.

When the receptor molecule grafted to the surface of the material (M) interacts with the target molecule, it makes the electrical signal vary. This variation may be a variation in conductance, current, transconductance, capacitance, threshold voltage or a combination thereof.

The electrical device may be a resistive device, or else a field-effect transistor type device.

When the electrical device is a resistive device, the variation in the current between the source and drain electrodes is detected and optionally measured, for example.

By way of example, in the case of a material (M) functionalized by grafting 4-ethynyltabinol, a variation in current is caused by the production of positive charges during the cyclization of the receptor molecule, when it makes contact with the organophosphorus compounds, at a given and known voltage applied across the source and drain electrodes. This current variation produces a conductance variation.

When the electrical device is of the transistor type, the semiconductor part is formed from a dielectric semiconductor material and in addition comprises a gate.

Here as well, the variation in current flowing through the transistor, at a given and known voltage applied across the source and drain electrodes, is detected and optionally measured, for example. Since the current is a function of the voltage on the gate, this then allows the transconductance of the transistor to be calculated.

In both cases, the variation in the conductance or the variation in transconductance is evidence of the presence of the compounds to be detected, and is proportional to their concentration.

Definitions

The term "nanowire" or "nanotube" is understood to mean a wire or a tube, respectively, having a diameter of less than 100 nm, especially of between 20 and 50 nm.

The term "nanosheet", is understood to mean a sheet having a thickness of less than 100 nm, especially of between 20 and 70 nm. The two other dimensions are in a ratio of greater than 2.

The expression "conductive material" is understood to mean an electrically conductive material, i.e. a material containing one or more mobile electric charges. Preferably, the conductive material has a resistance that is high enough for its heating to be used. More preferably, the resistance of the conductive material is greater than or equal to 1000 ohms.

The expression "semiconductor material" is understood to mean a material having an electrical conductivity lying between that of the metals and that of insulators.

BRIEF DESCRIPTION OF THE DRAWINGS

Figure:
FIG. 1 shows a schematic representation of the surface-functionalization method according to the invention.

DETAILED DESCRIPTION

EXAMPLES

Example 1

Selective Functionalization of a Silicon Nanosheet

Silicon Nanosheet Fabrication

Silicon nanowires were prepared using an SOI (silicon-on-insulator) wafer. The SOI wafer comprised a layer of boron-doped ($10^{15}$ at·cm$^{-3}$) single crystal silicon 70 nm in thickness on a buried oxide 140 nm in thickness. The Si wires were fabricated using e-beam lithography and RIE (reactive ion etching). A thin layer 45 nm in thickness of negative resist (HSQ FOX 12) was spun coated onto the clean and deoxidized SOI wafer. The resist was developed by immersing the substrate in a solution of 25% tetramethylammonium hydroxide in water (TMAOH) for 1 minute after exposure to an e-beam.

After reactive ion etching (RIE) using a 15 sccm $SF_6$/10 sccm $N_2$/10 sccm $O_2$ plasma (10 mT, 50 W, 80 s in an Oxford Instruments Plasmalab system), nanosheets of various lengths and widths (4×4 µm, 4×1 µm, 2×1 µm and 2×0.2 µm), connected to 30 µm×30 µm square pads of silicon, for the source and drain contacts, were obtained. Finally, the HSQ resist was removed by chemical etching (HF 1%, 1 min). The step reduced the thickness of the exposed $SiO_2$ to 134 nm. Large (100 µm×100 µm) metal contacts were defined on the 30 µm×30 µm silicon pads using e-beam lithography and two spun-coated resist layers (10% EL—17.5% MMA copolymer and 3% 495 K PMMA) having respective thicknesses of 610 nm and 60 nm. After exposure to an e-beam, the resist was developed in a solution of ⅓ methylisobutylketone (MIBK) and ⅔ isopropanol for 60 s. The metal layer (10 nm titanium and 100 nm gold) was then deposited using a vacuum e-beam evaporator. The lift-off step was then carried out in an acetone bath.

Selective Functionalization of a Nanosheet Using Ethynylferrocene

A potential of 5 V was applied across the source and drain electrodes of a nanosheet. The device was then immersed in a solution of (10 mM of) ethynylferrocene in mesitylene. Depending on the separation of the electrodes, the voltage applied lay between 2 and 10 V.

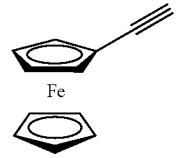

After rinsing in mesitylene and in dichloromethane, analysis using Auger, XPS and IR spectroscopy showed that only the connected nanosheet had been functionalized.

Selective Functionalization of a Nanosheet with a Receptor Specific to Organophosphorus Gases A potential of 5 V was applied across the source and drain electrodes of a nanosheet and the device was immersed in a (1 mM) 4-ethynyltabinol (structure above) in mesitylene solution.

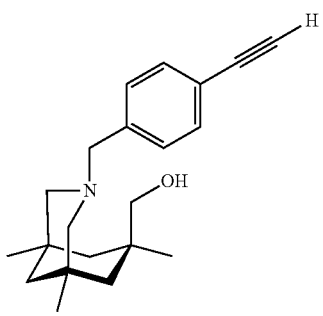

After rinsing in mesitylene and in dichloromethane, analysis using Auger, XPS and IR spectroscopy showed that only the connected nanosheet had been functionalized.

The invention claimed is:

1. A method for functionalizing a conductive or semiconductor material (M) by covalent grafting of receptor molecules (R) to its surface, said method comprising the following steps:
   i) applying, across the terminals of a source electrode and a drain electrode located on either side of the material (M), sufficient potential difference to thermally activate the material (M) with respect to the grafting reaction of the molecules (R); and
   ii) placing the material (M) thus activated in contact with a liquid or gaseous medium containing receptor molecules (R), thereby obtaining a material (M) functionalized by covalently grafted receptor molecules (R).

2. The method as claimed in claim 1, in which the material (M) is a semiconductor.

3. The method as claimed in claim 2, in which the semiconductor is a carbon-, silicon-, germanium-, zinc-, gallium-, indium- or cadmium-based material or an organic semiconductor.

4. The method as claimed in claim 3, in which the semiconductor is silicon based.

5. The method as claimed in claim 4, in which the material (M) comprises silicon nanowires or nanosheets.

6. The method as claimed in claim 3, in which the material (M) is carbon based.

7. The method as claimed in claim 6, in which the material (M) comprises carbon nanotubes or sheets.

8. The method as claimed in claim 4, in which the receptor molecules (R) comprise a $-C\equiv C-$ or $-HC=CH-$ group.

9. The method as claimed in claim 8, in which the receptor molecules are chosen from ethynylferrocene or 4-ethynyltabinol.

10. The method as claimed in claim 6, in which the receptor molecules comprise a diazonium salt, a triazene or a diene.

11. The method as claimed in claim 10, in which the receptor molecules are chosen from diazoniumferrocene or 4-diazobenzyltabinol.

* * * * *

UNITED STATES PATENT AND TRADEMARK OFFICE
CERTIFICATE OF CORRECTION

PATENT NO.       : 8,389,325 B2  
APPLICATION NO.  : 13/180754  
DATED            : March 5, 2013  
INVENTOR(S)      : Carella et al.

Page 1 of 1

It is certified that error appears in the above-identified patent and that said Letters Patent is hereby corrected as shown below:

In the Specification

<u>Column 1,</u>  
Line 61, "Nano Leu." should read --Nano Lett.--.

Signed and Sealed this  
Eleventh Day of June, 2013

Teresa Stanek Rea  
*Acting Director of the United States Patent and Trademark Office*